US012159420B2

United States Patent
Pati et al.

(10) Patent No.: US 12,159,420 B2
(45) Date of Patent: Dec. 3, 2024

(54) METHODS AND SYSTEMS FOR IMAGE REGISTRATION

(71) Applicant: GE Precision Healthcare LLC, Waukesha, WI (US)

(72) Inventors: Dibyajyoti Pati, San Ramon, CA (US); Junpyo Hong, San Ramon, CA (US); Venkata Ratnam Saripalli, Danville, CA (US); German Guillermo Vera Gonzalez, Waukesha, WI (US); Dejun Wang, Beijing (CN); Aizhen Zhou, Beijing (CN); Gopal B. Avinash, San Ramon, CA (US); Ravi Soni, San Ramon, CA (US); Tao Tan, Nuenen (NL); Fuqiang Chen, Beijing (CN); Yaan Ge, Beijing (CN)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 333 days.

(21) Appl. No.: 17/457,179

(22) Filed: Dec. 1, 2021

(65) Prior Publication Data
US 2023/0169666 A1 Jun. 1, 2023

(51) Int. Cl.
G06T 7/30 (2017.01)
A61B 6/00 (2006.01)
G06N 3/08 (2023.01)

(52) U.S. Cl.
CPC .............. *G06T 7/30* (2017.01); *A61B 6/5241* (2013.01); *G06N 3/08* (2013.01);
(Continued)

(58) Field of Classification Search
CPC .................... A61B 6/5241; G06N 3/08; G06T 2207/10116; G06T 2207/20081;
(Continued)

(56) References Cited

U.S. PATENT DOCUMENTS 8,737,708 B2 5/2014 Hartmann et al.
9,713,506 B2 7/2017 Fanson et al.
(Continued)

FOREIGN PATENT DOCUMENTS

CN 103839265 A 6/2014
EP 3121789 A1 1/2017
(Continued)

OTHER PUBLICATIONS

Meng X et al, Resnet-based Quality Evaluation of Image Mosaic and Training Data Balance, 2021, 2021 International Conference on Advances in Computer Technology, Information Science and Communication, pp. 1-8. (Year: 2021).*
(Continued)

*Primary Examiner* — Aaron W Carter
*Assistant Examiner* — Kathleen M Broughton
(74) *Attorney, Agent, or Firm* — McCoy Russell LLP

(57) ABSTRACT

Various methods and systems are provided for automatically registering and stitching images. In one example, a method includes entering a first image of a subject and a second image of the subject to a model trained to output a transformation matrix based on the first image and the second image, where the model is trained with a plurality of training data sets, each training data set including a pair of images, a mask indicating a region of interest (ROI), and associated ground truth, automatically stitching together the first image and the second image based on the transformation matrix to form a stitched image, and outputting the stitched image for display on a display device and/or storing the stitched image in memory.

20 Claims, 8 Drawing Sheets

(52) U.S. Cl.
CPC ............... *G06T 2207/10116* (2013.01); *G06T 2207/20081* (2013.01); *G06T 2207/20084* (2013.01); *G06T 2207/20212* (2013.01)

(58) Field of Classification Search
CPC . G06T 2207/20084; G06T 2207/20212; G06T 2207/10016; G06T 2207/20104; G06T 2207/30012; G06T 2207/30052; G06T 2200/32; G06T 3/4038; G06T 7/30; G06T 7/73; G06V 10/25
See application file for complete search history.

(56) References Cited

U.S. PATENT DOCUMENTS

| | | | |
|---|---|---|---|
| 10,503,868 | B2 | 12/2019 | Chukka et al. |
| 2015/0023575 | A1* | 1/2015 | Valadez ................... G06T 7/11 382/131 |
| 2017/0111581 | A1* | 4/2017 | Muenzenmayer ... H04N 13/117 |
| 2017/0337682 | A1* | 11/2017 | Liao ...................... A61B 5/7267 |
| 2019/0000564 | A1* | 1/2019 | Navab .................. H04N 13/254 |
| 2020/0202515 | A1* | 6/2020 | Prasad ..................... G06T 7/33 |

FOREIGN PATENT DOCUMENTS

| | | |
|---|---|---|
| EP | 3246875 A2 | 11/2017 |
| WO | 2019012520 A1 | 1/2019 |

OTHER PUBLICATIONS

Li A et al, Image Stitching Based on Planar Region Consensus, 2020, arXiv:2007.02722v1, pp. 1-17. (Year: 2020).*

Huang H et al, Semantic Segmentation Guided Feature Point Classification and Seam Fusion for Image Stitching, J. Algorithms & Computational Technology (15): 1-12. (Year: 2021).*

Sun H et al, Stepwise Local Stitching Ultrasound Image Algorithms Based on Adaptive Iterative Threshold Harris Corner Features, Medicine 99 (37): 1-8. (Year: 2020).*

Yan et al, Image stitching with single-hidden layer feedforward neural networks, 2016 IEEE International Joint Conference on Neural Networks, pp. 1-8. (Year: 2016).*

Liu et al, Research on Panoramic Stitching Algorithm of Lateral Cranial Sequence Images in Dental Multifunctional CBCT, Sensors 21(2100): 1-19. (Year: 2021).*

EP application 22207646.5 filed Nov. 15, 2022—extended Search Report issued May 2, 2023; 10 pages.

Rocco, I. et al., "Convolutional neural network architecture for geometric matching," Proceedings of the IEEE Conference on Computer Vision and Pattern Recognition (CVPR), Jun. 17, 1997, San Juan, Puerto Rico, 10 pages.

Li, H. et al., "Non-rigid registration using fully convolutional networks with deep self-supervision," arXiv Cornell University Website, Available Online at https://arxiv.org/abs/1709.00799, Available as Early as Sep. 4, 2017, 8 pages.

Sokooti, H. et al., "Nonrigid Image Registration Using Multi-scale 3D Convolutional Neural Networks," Proceedings of the International Conference on Medical Image Computing and Computer-Assisted Intervention (MICCAI 2017), Sep. 11, 2017, Quebec City, QC, Canada, 8 pages.

Sloan, J. et al., "Learning Rigid Image Registration-Utilizing Convolutional Neural Networks for Medical Image Registration," Proceedings of the 11th International Joint Conference on Biomedical Engineering Systems and Technologies, Jan. 19, 2018, Funchal, Madeira, Portugal, 11 pages.

Balakrishnan, G. et al., "VoxelMorph: A Learning Framework for Deformable Medical Image Registration," arXiv Cornell University Website, Available Online at https://arxiv.org/abs/1809.05231, Available as Early as Sep. 14, 2018, 16 pages.

Haskins, G. et al., "Deep Learning in Medical Image Registration: A Survey," arXiv Cornell University Website, Available Online at https://arxiv.org/abs/1903.02026, Available as Early as Mar. 5, 2019, 30 pages.

* cited by examiner

METHODS AND SYSTEMS FOR IMAGE REGISTRATION

FIELD

Embodiments of the subject matter disclosed herein relate to medical imaging.

BACKGROUND

Imaging technologies such as x-ray imaging allow for non-invasive acquisition of images of internal structures or features of a subject, such as a patient. Digital x-ray imaging systems produce digital data which can be processed into radiographic images. In digital x-ray imaging systems, radiation from a source is directed toward the subject. A portion of the radiation passes through the subject and impacts a detector. The detector includes an array of discrete picture elements or detector pixels and generates output signals based upon the quantity or intensity of the radiation impacting each pixel region. The output signals are subsequently processed to generate an image that may be displayed for review. These images are used to identify and/or examine the internal structures and organs within a patient's body. In some instances, multiple images may be used to capture a single structure or region of interest. The multiple images may be captured under the same or under different conditions, for example, patient position, radiation dose, and so on.

BRIEF DESCRIPTION

Embodiments for registering images are provided herein. In one example, a method includes entering a first image of a subject and a second image of the subject to a model trained to output a transformation matrix based on the first image and the second image, where the model is trained with a plurality of training data sets, each training data set including a pair of images, a mask indicating a region of interest (ROI), and associated ground truth. The method further includes automatically stitching together the first image and the second image based on the transformation matrix to form a stitched image, and outputting the stitched image for display on a display device and/or storing the stitched image in memory.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
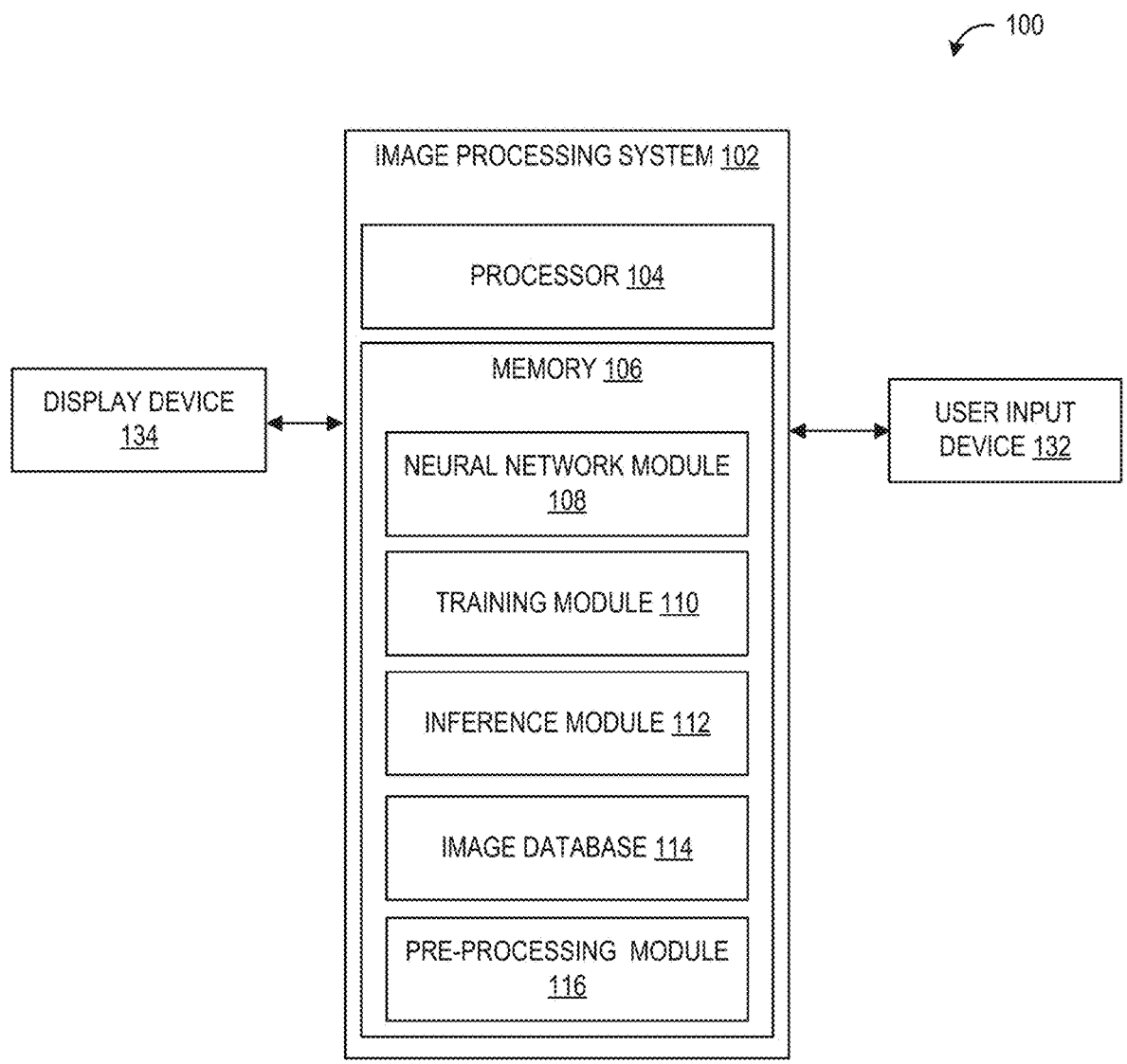
FIG. 1 shows a block diagram of an exemplary embodiment of an image processing system.

The following description relates to various embodiments of a method for training and implementing a deep learning model, such as a convolutional neural network (CNN), to output a transformation matrix based on correspondence of image pairs and automatically stitching together images of the image pairs based on the transformation matrix to form a stitched image.

Some imaging protocols, such as X-ray imaging protocols for imaging the spine or one or more leg bones (e.g., femur), include the acquisition of two overlapping images that are then stitched together to create a stitched image showing a full extent of a desired anatomical feature than cannot be imaged with a single image. Traditional mechanisms for automatically stitching together two overlapping images may include search-based methods, where a common anatomical feature between the overlapping images is identified and used as a basis for stitching the images. However, these approaches often result in mis-registration of the images when lateral motion occurs between acquisition of the images (e.g., such that the anatomical features in one image are laterally offset from the anatomical features of the other image). Further, these approaches may have difficulty registering and stitching images when a low amount of overlap is present between the images (e.g., less than 5 cm), when non-rigid artifacts such as stomach gas are present, or when the images are acquired with different X-ray dose levels.

Thus, according to embodiments disclosed herein, a deep learning model, such as the CNN as described above, may be trained to output a transformation matrix that can be used to stitch together two images, where the deep learning model is trained to output an accurate transformation matrix even in the presence of large lateral or vertical motion between images, non-rigid or rigid artifacts in the images, varying dose levels, and low overlap. In some embodiments, the deep learning model is trained with a plurality of training data sets, each including two training pairs and associated ground truth. Together, the training pairs may include an image pair comprised of a first image and a second image, where the first image has a first field of view (FOV) and the second image has a second FOV. Each of the first image and the second image may capture a region of interest (ROI)

where the FOVs at least partially overlap. The ROI may be a rigid structure, such as a rigid anatomical feature (e.g., spine, tibia) or an implant. The training pairs may further comprise one or more masks, where a first mask is generated based on the first image and/or a second mask is generated based on the second image. Each mask may be configured to identify the ROI that should be used for registering the images. As a result, a transformation matrix may be generated by the model. The transformation matrix may include one or more of horizontal shifts, vertical shifts, rotation, skew, and zoom functions. The generated transformation matrix may then be compared to the associated ground truth, and loss may be calculated using two or more loss functions. Calculated loss may then be used to refine the deep learning model. The deep learning model may be further refined using augmented training data sets. By training the deep learning model using the plurality of training data sets, augmented training data sets, and multiple loss functions, the trained deep learning model may be tolerant of lateral motion, non-rigid artifacts, foreign objects, dose invariance, and so on.

The trained deep learning model may then be implemented to output a transformation matrix used to stitch together an image pair (e.g., a first image and a second image showing a common ROI and having partially overlapping FOVs) into a single image including the full ROI. By nature of the ROI being a rigid structure, generating a transformation matrix based on the ROI may be more accurate than if a ROI were soft tissue, which may shift position between capture of the first image and the second image.

In this way, a general purpose image stitching system may be created which is tolerant of, and therefore may stitch together images including at least one of, lateral motion, non-rigid artifacts, foreign objects, dose invariance, and so on such that the ROI and other elements of the first image and the second image may not be distorted in the stitched image.

Figure 2:
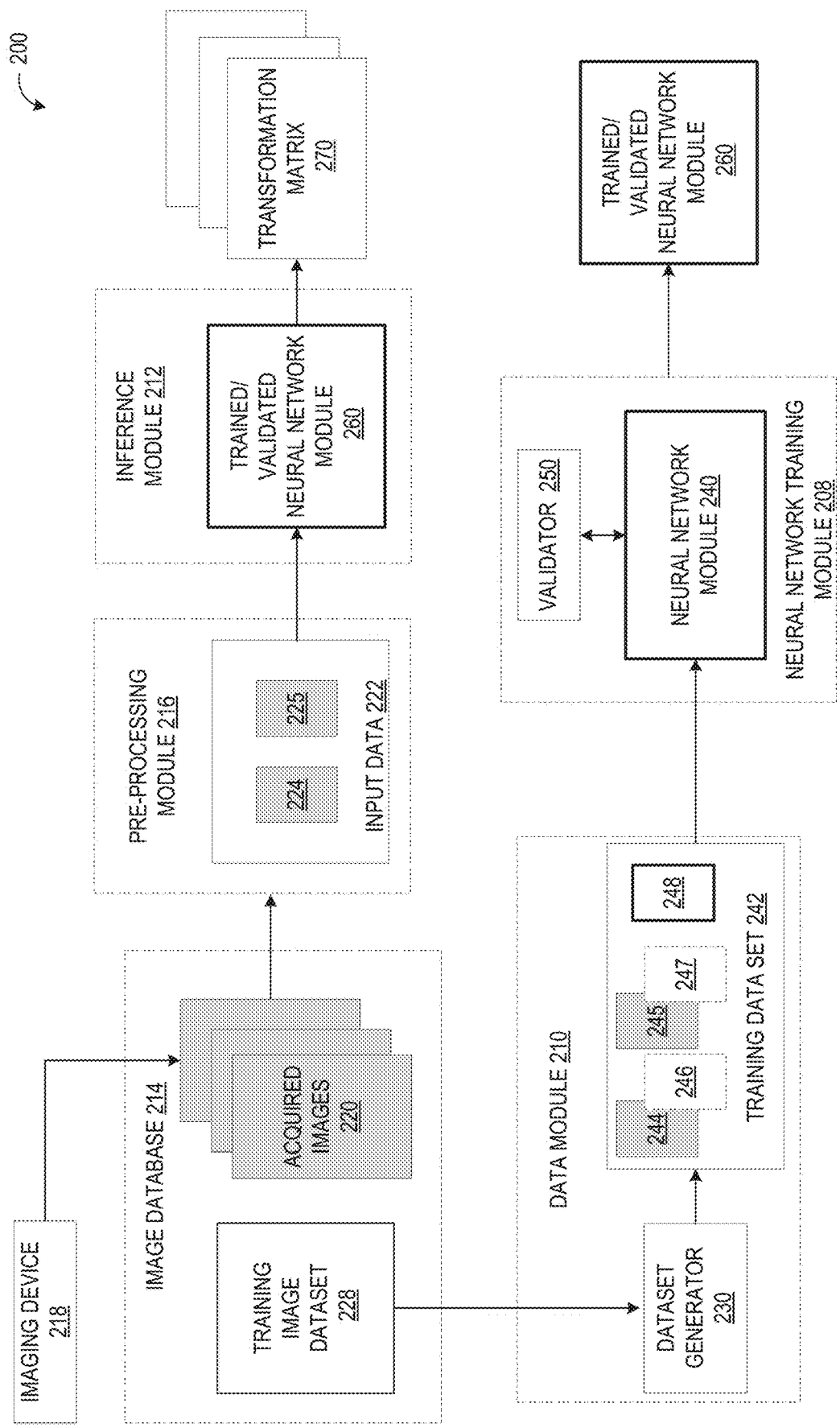
FIG. 2 shows a block diagram of an exemplary embodiment of a transformation matrix prediction network (TMPN) training and implementation system.
Figure 3A:
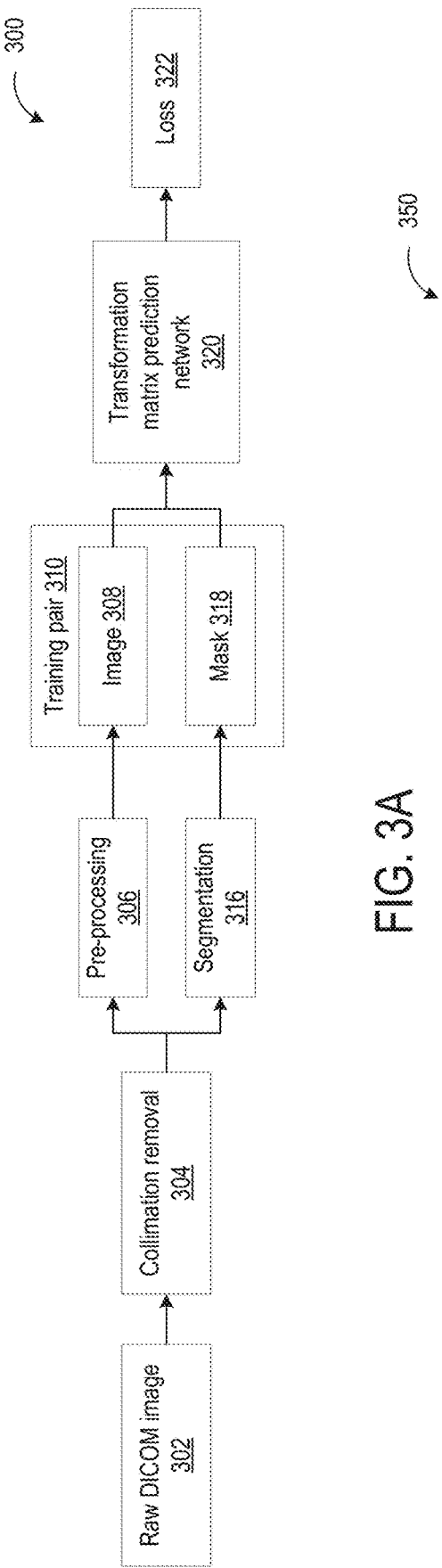
FIG. 3A shows a first example workflow for training the TMPN.
Figure 3B:
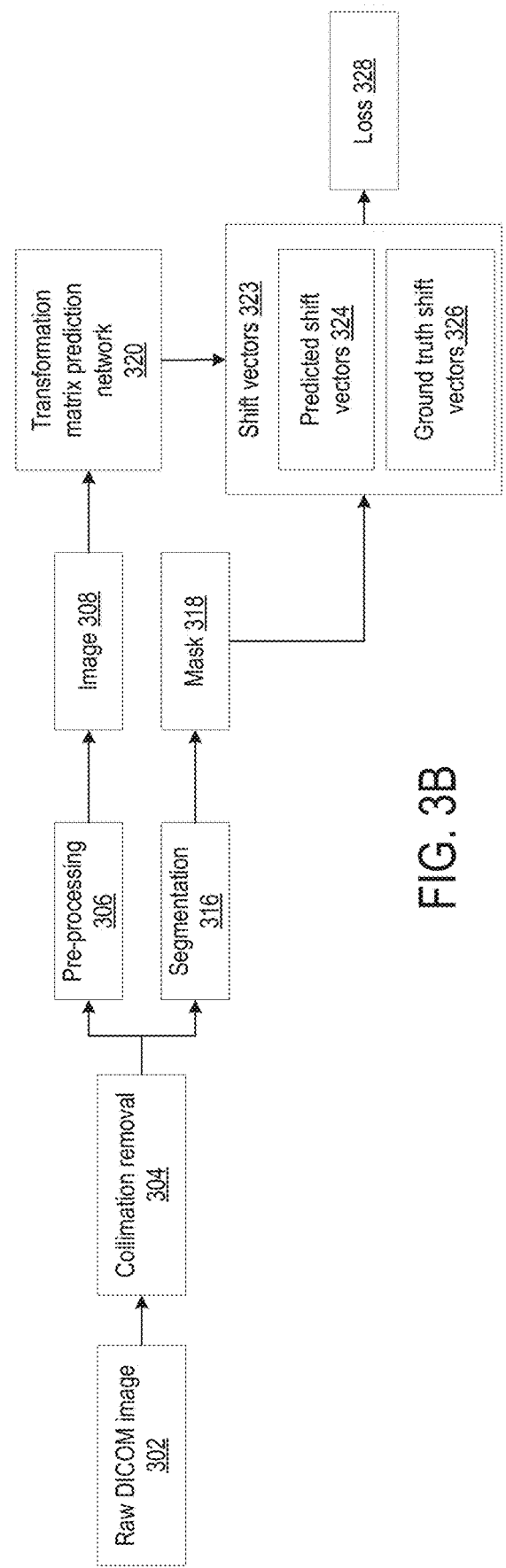
FIG. 3B shows a second example workflow for training the TMPN.
Figure 4:
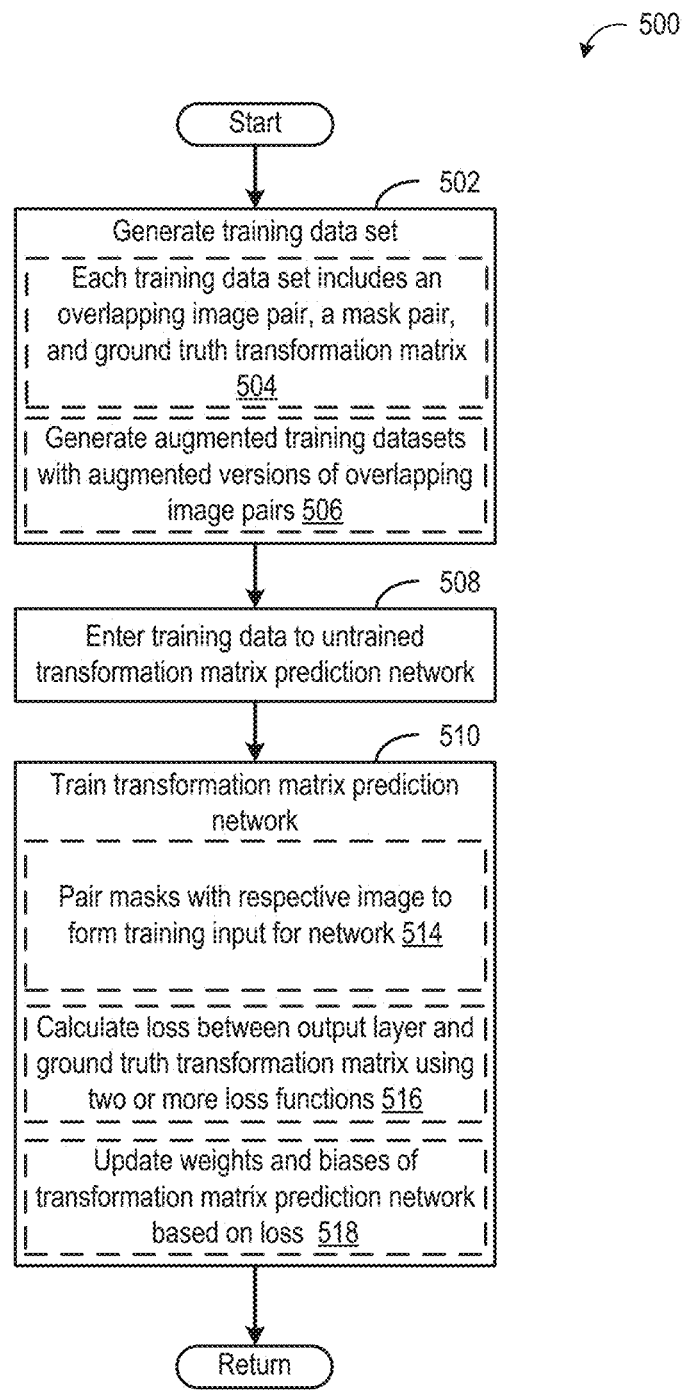
FIG. 4 shows flow chart of an example method for training the TMPN to generate a transformation matrix based on input data.
Figure 5:
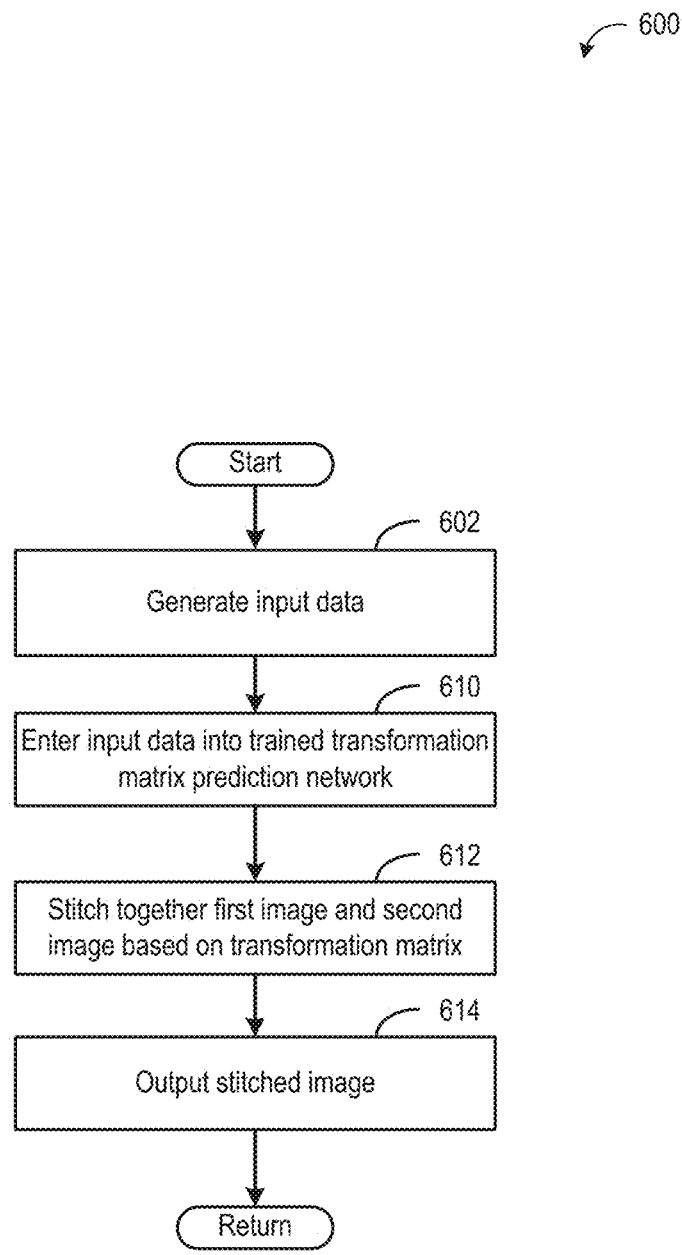
FIG. 5 shows a flow chart of an example method for implementing the trained TMPN.

A block diagram of an exemplary embodiment of an image processing system is shown in FIG. 1. The image processing system of FIG. 1 includes a neural network module configured with a neural network, such as a CNN or a Siamese twin network, which may be trained and deployed by other modules of the image processing system to output a transformation matrix based on a first image of a subject and a second image of the subject. The neural network may thus be referred to as a transformation matrix prediction network (TMPN). The transformation matrix may be used to automatically stitch together the first image and the second image, where each of the first image and the second image capture different views of a region of interest (ROI) such that the resulting stitched image includes the full ROI. A high-level workflow describing methods for training and implementing the TMPN is shown in FIG. 2. A first example method for generating a training pair for training the TMPN is shown in FIG. 3A. Training pairs may be input into the TMPN to generate a transformation matrix, wherein the transformation matrix is comprised of shift vectors (e.g., horizontal shifts, vertical shifts, rotation, skew, and zooming) generated using multiple training pairs. Loss may then be calculated by comparing a stitched image generated using the transformation matrix, and a ground truth transformation matrix, as shown in FIG. 2. A second example method for training the TMPN is shown in FIG. 3B, wherein images are input to the TMPN to generate predicted shift vectors. The predicted shift vectors are compared to ground truth shift vectors, and respective masks of the images are applied to the predicted shift vectors and ground truth shift vectors to scale calculated loss to a ROI. Loss calculated using the methods of FIGS. 3A-3B may be used to refine the TMPN using a validator shown in FIG. 2. FIG. 4 shows a flow chart of an example method for training the TMPN to generate a transformation matrix based on training data, which includes training pairs optionally including respective masks, as described in FIGS. 3A-3B. FIG. 5 shows a flow chart of an example method for implementing the trained TMPN to generate a transformation matrix, stitch input images based on the transformation matrix, and output the stitched image.

Figure 6A:
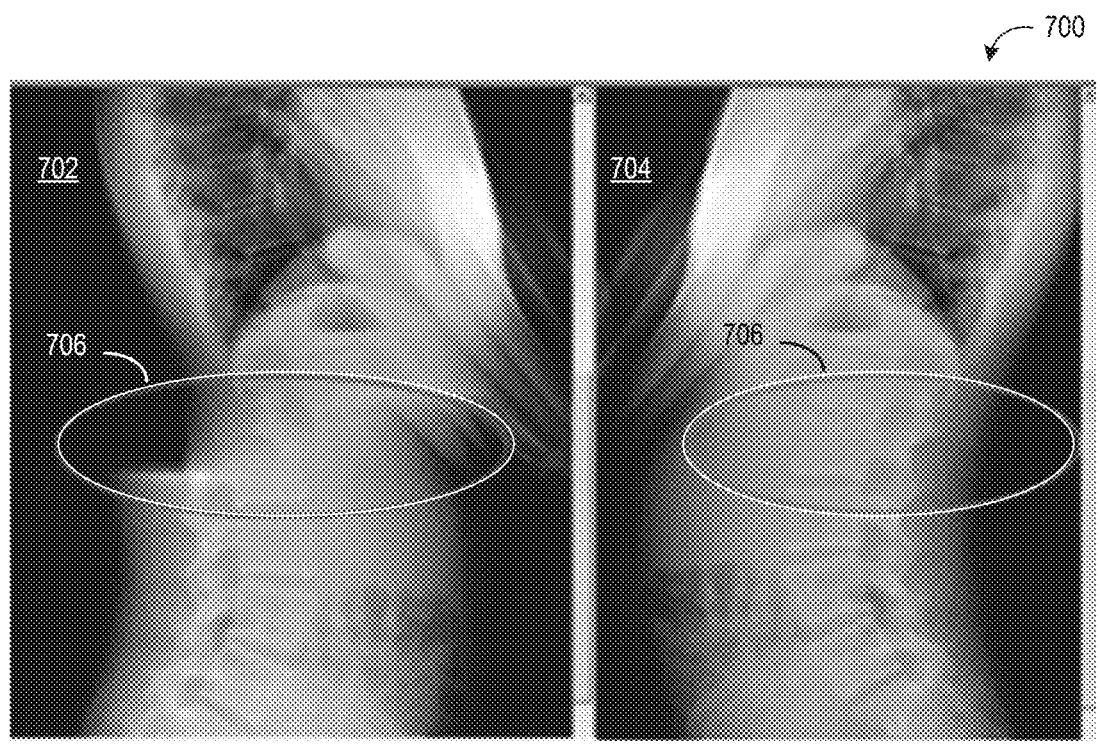
FIG. 6A shows example images comparing auto-pasting and manual pasting for a pair of X-ray images with lateral motion.
Figure 6B:
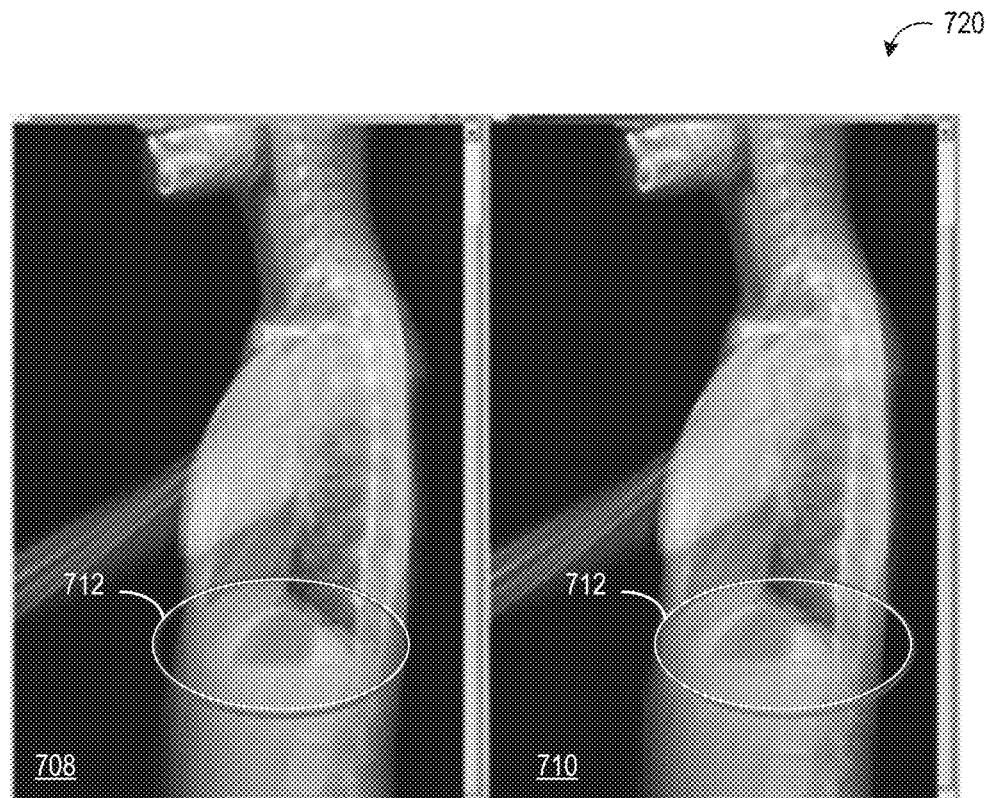
FIG. 6B show example images comparing auto-pasting and manual pasting for a pair of X-ray images including non-rigid artifacts.
Figure 6C:
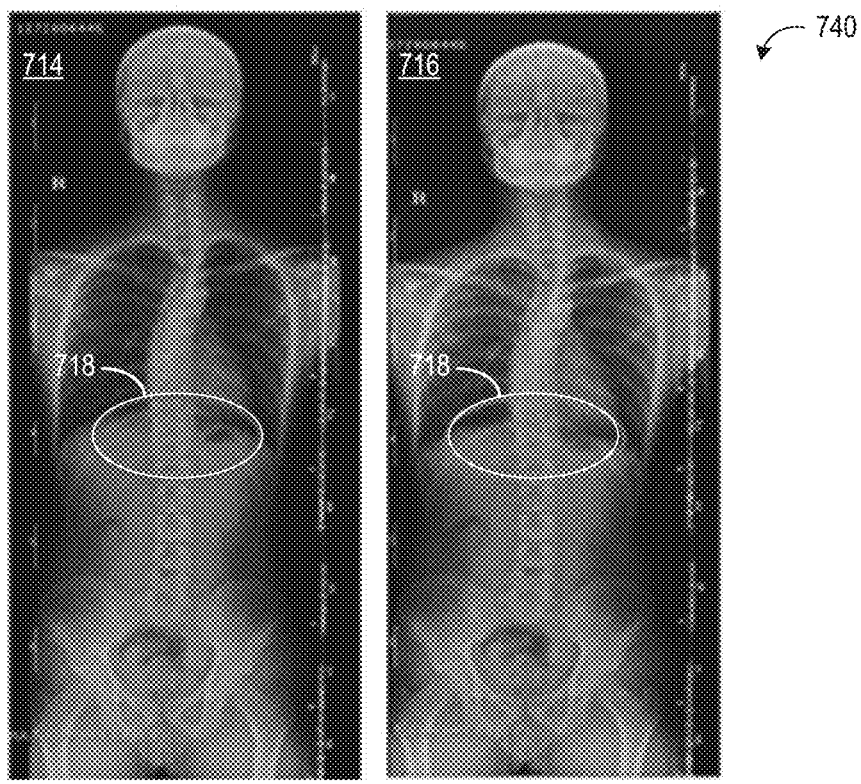
FIG. 6C shows example images comparing auto-pasting and manual pasting for a pair of X-ray images taken using an incorrect protocol selection.
Figure 6D:
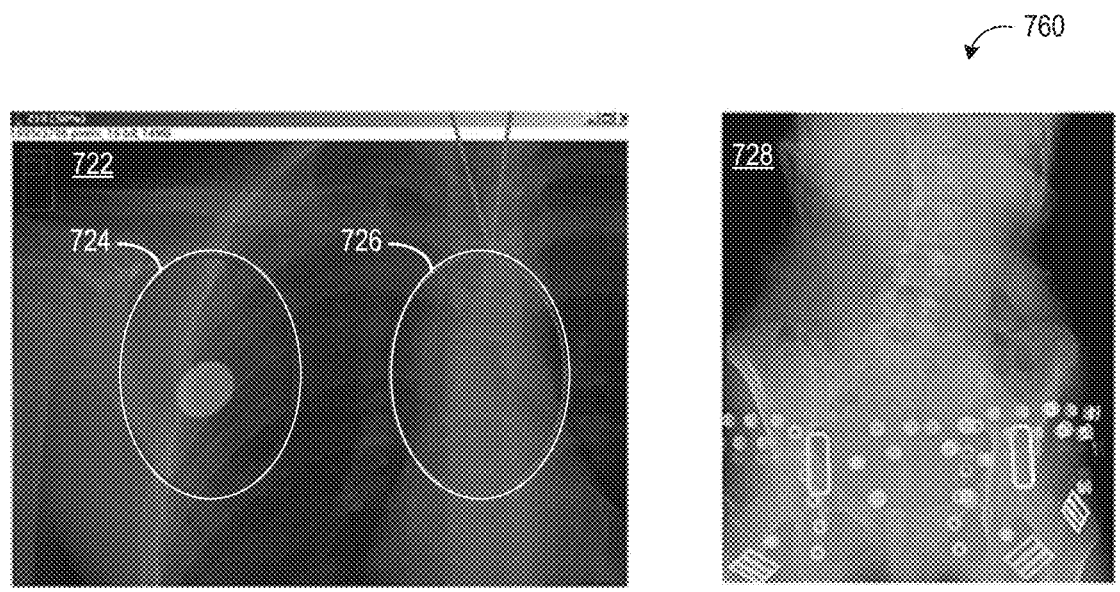
FIG. 6D show example X-ray images including foreign objects.
Figure 7:
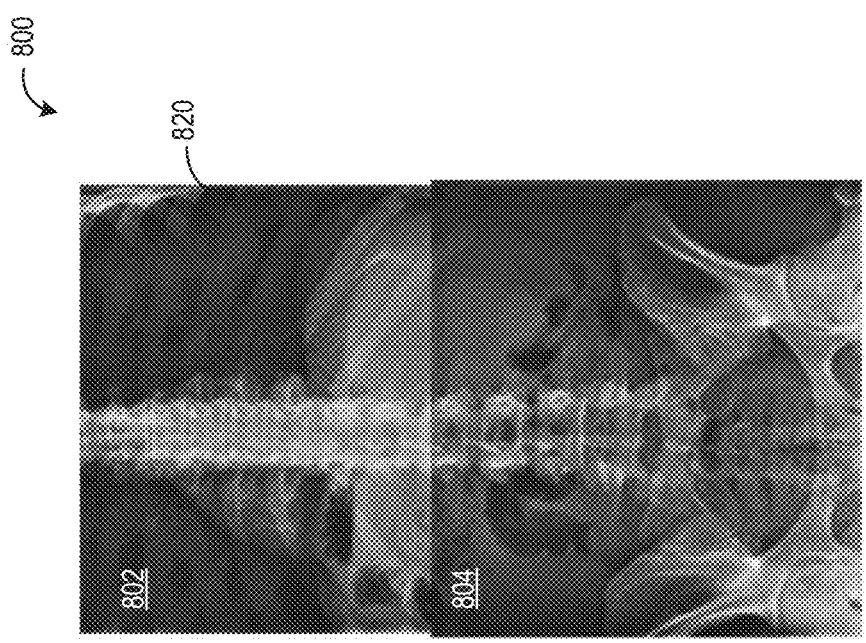
FIG. 7 shows example images comparing an input image pair and a resulting stitched image, according to the method of the disclosure.
Figure 7:
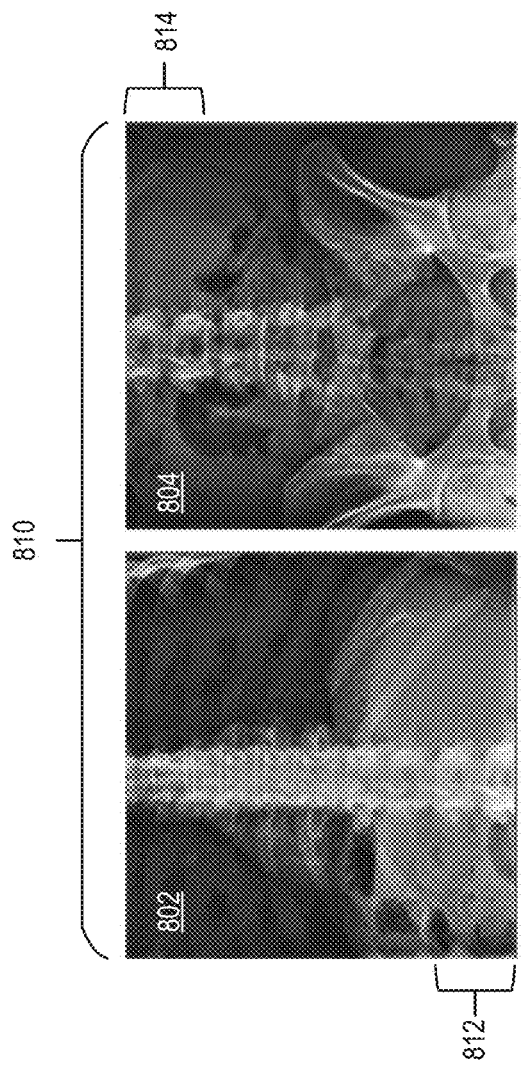

FIGS. 6A-6D show stitched images comparing conventional methods for image-auto pasting and manual pasting methods. FIG. 6A compares auto-pasted and manually-pasted images where there is lateral motion during or between image captures exceeding a lateral motion tolerance of the image auto-pasting method. FIG. 6B compares auto-pasted and manually-pasted images where the images include non-rigid artifacts, such as stomach gas. FIG. 6C compares auto-pasted and manually-pasted images where an incorrect protocol is selected for image auto-pasting. FIG. 6D compares auto-pasted and manually-pasted images where the images include foreign objects. The TMPN may be trained to tolerate the aforementioned challenges and stitch images resembling those stitched using manual pasting methods. FIG. 7 shows an example implementation of the trained TMPN described herein, where a first image and a second image may be stitched into a single image using a transformation matrix generated by the trained TMPN.

FIG. 1 shows a block diagram 100 of an exemplary embodiment of an image processing system 102 in accordance with an embodiment. In some embodiments, image processing system 102 is incorporated into an X-ray imaging system. For example, image processing system 102 may be provided in an X-ray imaging system as a processor and memory of the X-ray imaging system. In some embodiments, at least a portion of image processing system 102 is disposed at a device (e.g., edge device, server, etc.) communicably coupled to the X-ray imaging system via wired and/or wireless connections. In some embodiments, at least a portion of image processing system 102 is disposed at a separate device (e.g., a workstation) which can receive images from the X-ray imaging system or from a storage device which stores the images/data generated by the X-ray imaging system. Image processing system 102 may be operably/communicatively coupled to a user input device 132 and a display device 134. User input device 132 may comprise a user interface of an X-ray imaging system while display device 134 may comprise a display device of the X-ray imaging system, at least in some examples. In some embodiments, user input device 132 and display device 134 may be disposed at a separate device (e.g., a workstation) which can receive images from the X-ray imaging system or from a storage device which stores the images/data generated by the X-ray imaging system.

Image processing system 102 includes a processor 104 configured to execute machine readable instructions stored in memory 106. Processor 104 may be single core or multi-core, and the programs executed thereon may be configured for parallel or distributed processing. In some embodiments, processor 104 may optionally include individual components that are distributed throughout two or more devices, which may be remotely located and/or configured for coordinated processing. In some embodiments, one or more aspects of processor 104 may be virtualized and executed by remotely-accessible networked computing devices configured in a cloud computing configuration.

Memory 106 may store a neural network module 108, a training module 110, an inference module 112, an image database 114, and a pre-processing module 116. In some embodiments, as further described herein, the pre-processing module 116 may include two modules, comprising a pre-processing module and a segmentation module. Neural network module 108 may include at least a deep learning model (e.g., a deep learning (DL) neural network), such as a CNN, and instructions for implementing the neural network to output a transformation matrix based on input pairs, as described in greater detail below. Neural network module 108 may include trained and/or untrained neural networks and may further include various data, or metadata pertaining to the one or more neural networks stored therein.

Memory 106 may further store a training module 110, which may comprise instructions for training one or more of the neural networks stored in neural network module 108. Training module 110 may include instructions that, when executed by processor 104, cause image processing system 102 to conduct one or more of the steps of method 500 for generating a training data set for training a neural network model, discussed in more detail below in reference to FIG. 4. Workflows 300 and 350 of FIGS. 3A-3B, respectively, provide additional or alternative methods for training the neural network model. In some embodiments, training module 110 may include instructions for implementing one or more gradient descent algorithms, applying one or more loss functions, and/or training routines, for use in adjusting parameters of one or more neural networks of neural network module 108. Training module 110 may include training datasets for the one or more neural networks of neural network module 108. In some examples, training module 110 may be located on a different device than the image processing system, for example, an edge device, server, or workstation communicatively coupled with the image processing system.

Memory 106 also stores an inference module 112. Inference module 112 may include instructions for deploying a trained deep learning model (e.g., CNN) to generate a transformation matrix based on input pairs. In particular, inference module 112 may include instructions that, when executed by processor 104, cause image processing system 102 to conduct one or more of the steps of the method 600 of FIG. 5, as described in further detail below.

Memory 106 further stores image database 114. Image database 114 may include, for example, X-ray images acquired via an X-ray imaging system. Image database 114 may include one or more training sets for training the one or more neural networks of neural network module 108. In some examples, the image database 114 may be located on a different device than the image processing system, for example, an edge device, server, or workstation communicatively coupled with the image processing system.

Memory 106 further stores pre-processing module 116. In some embodiments, as further described in FIGS. 3A-3B, the pre-processing module 116 may be two separate modules, comprising a pre-processing module and a segmentation module. The pre-processing module and segmentation module may include instructions for pre-processing and segmenting acquired images, respectively, such as images stored in image database 114. As further described in FIGS. 3A-3B, the pre-processing module and segmentation module, independently or in tandem, may respectively generate an image and a mask from the acquired image to be used for generating a transformation matrix and/or calculating loss to train the neural network model.

In some embodiments, memory 106 may include components disposed at two or more devices, which may be remotely located and/or configured for coordinated processing. In some embodiments, one or more aspects of memory 106 may include remotely-accessible networked storage devices configured in a cloud computing configuration.

User input device 132 may comprise one or more of a touchscreen, a keyboard, a mouse, a trackpad, a motion sensing camera, or other device configured to enable a user to interact with and manipulate data within image processing system 102. In one example, user input device 132 may enable a user to make a selection of an image to use in training a machine learning model, or for further processing using a trained machine learning model.

Display device 134 may include one or more display devices utilizing virtually any type of technology. In some embodiments, display device 134 may comprise a computer monitor, and may display ultrasound images. Display device 134 may be combined with processor 104, memory 106, and/or user input device 132 in a shared enclosure, or may be peripheral display devices and may comprise a monitor, touchscreen, projector, or other display device known in the art, which may enable a user to view X-ray images produced by an X-ray imaging system, and/or interact with various data stored in memory 106.

It should be understood that image processing system 102 shown in FIG. 1 is for illustration, not for limitation. Another appropriate image processing system may include more, fewer, or different components.

Referring to FIG. 2, an example of a training and implementation system 200 for a transformation matrix prediction network (TMPN) is shown. Training and implementation system 200 may be implemented by one or more of an image processing system, such as image processing system 102 of FIG. 1, to train a DL neural network, such as a CNN, to generate a transformation matrix based on input pairs. In an embodiment, training and implementation system 200 includes a neural network module 240, to be trained, which may be a part of a neural network training module 208 of the image processing system. Although described herein as one system, a training workflow and an implementation workflow of the training and implementation system 200 may be separate workflows and may be stored on different systems and implemented by different modules, as further described herein. The neural network module 240 may be trained on a plurality of training data sets, which may be stored in a data module 210. Each training data set 242 may comprise a plurality of training pairs and ground truth target data.

In an embodiment, each training pair may comprise a first image and a first mask based on the first image. For example, a first training pair includes a first image 244 and a first mask 246. A second training pair includes a second image 245 and a second mask 247. The first image 244 and the second image 245 may be medical images acquired by an imaging device. For example, the medical images may be X-ray images acquired by an X-ray imaging system during an examination of one or more anatomical structures of a patient. Each of the first image 244 and the second image 245 may capture different views of a region of interest (ROI), such as an anatomical structure (e.g., spine). For example, the ROI may be a rigid structure present in both the first image 244 and the second image 245. In another example, the ROI may be identified based on a selected imaging protocol, where the selected imaging protocol indicates a predefined region, such as a spine, tibia, rib, and so on, which is at least partially present in both the first image 244 and the second image 245. Further, the first image 244 may capture a first field of view (FOV) of the subject and the second image 245 may capture a second FOV of the subject, wherein the first FOV and the second FOV partially overlap and each of the first FOV and the second FOV partially or fully include the ROI. Stitching of the first image 244 and the second image 245 therefore may generate a single image including the full ROI, as further described herein.

The first image 244, the first mask 246, the second image 245, and the second mask 247 of the training data set 242 may be obtained from a training image dataset 228. Training image dataset 228 may be an image dataset of the image processing system generated from examinations performed on subjects, or training image dataset 228 may be an external image dataset such as a public dataset of medical images. Training image dataset 228 may be stored in an image database 214, such as the image database 114 of FIG. 1.

In various embodiments, the first image 244, the first mask 246, the second image 245, and the second mask 247 may be selected and grouped as training data set 242 by a dataset generator 230. Dataset generator 230 may generate training data sets by selecting a first image (e.g., the first image 244) and a second image (e.g., the second image 245) where the first image and the second image include the same ROI and overlap by at least a certain overlap amount, and assigning the first image as the first image 244 and the second image as the second image 245. Further, the dataset generator 230 may pre-process the first image 244 and the second image 245 to reduce differences and increase correspondence between the first image and the second image, as described in FIGS. 3A-3B.

The first mask 246 may be generated based on the first image 244 and the second mask 247 may be generated based on the second image 245. Each of the first mask 246 and the second mask 247 may be generated by a segmentation model, computer vision, or user annotation, as further described herein. The dataset generator 230 may segment the first image 244 and the second image 245 to generate the first mask 246 and the second mask 247 based on respective images. Segmentation may be performed by an AI-based model (e.g., a neural network) trained to identify the ROI of an image and "segment" the ROI within the image. The segmentation module may be specific to a single type of ROI (e.g., spine, leg bone, implant). For example, a type of ROI of the images may be selected by a user of the image processing system (e.g., based on a selected scan protocol). The segmentation module may then identify and segment the ROI of each image. The image processing system may be configured to detect when an incorrect scanning protocol has been selected, for example, when a mask may not be generated by segmenting an image because the selected segmentation model is for a different ROI than is present in the image. For example, the first mask 246 may be generated based on the first image 244, where the first mask 246 is configured to identify the ROI. The second mask 247 may be generated based on the second image 245, where the second mask 247 is configured to identify the ROI. Alternatively, masks may be generated by user annotation or a computer-vision based model.

The masks may include a certain pixel value for all pixels in the ROI (e.g., a pixel value of 1) and a different pixel value for all pixels outside the ROI (e.g., a pixel value of zero). The masks may be entered as input to the model with the first image 244 and the second image 245, for example the first mask 246 may be concatenated with the first image 244 and the second mask 247 may be concatenated with the second image 245, such that each input comprises two layers, one layer including the image pixel values and the other layer including the mask values. The mask layer may inform the neural network module 240 that spatially corresponding pixel values from the image (e.g., in the ROI as defined by the mask) are more important for determining the transformation matrix. In other examples, each mask may inform the neural network module not to evaluate certain regions of the image (e.g., outside the ROI as defined by the mask). In this way, the network may be trained to only apply filters to sections of the image which contain at least some of the ROI. In still further examples, only one mask may be used (e.g., the first mask 246).

Additionally, the training pairs (e.g., the first training pair and the second training pair) of the training data set 242 may be assigned a ground truth 248. The ground truth 248 of the training data set 242 may be a ground truth transformation matrix, where the transformation matrix comprises shift vectors indicating horizontal shift and/or vertical shift, skew, zoom, and/or rotation which may be applied to at least one of the first image 244 and the second image 245 to stitch together the first image 244 and the second image 245 without distortion of the ROI.

Training and implementation system 200 may be used to train the neural network module 240 to learn to identify correspondence among input images (e.g., a ROI partially present in each of the input images) and predict a transformation matrix for facilitating stitching of the input images. In one example, neural network module 240 may be stored in the neural network training module 208 and be configured to receive the training data set 242 from the data module 210, where the first image 244, the first mask 246, the second image 245, and the second mask 247 are input into neural network module 240 to generate a transformation matrix (e.g., including shift vectors) based thereon. The generated transformation matrix and the ground truth 248 may be used to refine the neural network module 240, further described in FIG. 3A. In a second example, the first image 244 and the second image 245 are input into the neural network module 240 to generate a predicted transformation matrix, and the first mask 246 and the second mask 247 may be used to scale calculated loss between the ground truth 248 and the predicted transformation matrix, as further described in FIG. 3B.

The neural network training module 208 may further include a validator 250 that validates a performance of neural network module 240. Validator 250 may take as input a partially trained neural network module 240, an output (e.g., the transformation matrix based on training data set 242) of the neural network module 240, and training data set 242, including ground truth 248 (e.g., ground truth transformation matrix). The validator 250 may use the transformation matrix to stitch the first image (e.g., the first image 244) and the second image (e.g., the second image 245) to generate a stitched image. The validator 250 may then compare the stitched image to the ground truth 248 to calculate loss, and use calculated loss to adjust weights and biases of the neural network module 240. In another example, the validator 250 may compare the transformation matrix to ground truth 248 (e.g., ground truth transformation matrix) to calculate loss, and use calculated loss to adjust weights and biases of the neural network module 240.

For example, a partially trained neural network module 240 of an image processing system may be validated with a test dataset of 50 sets of training data set 242, where each of the 50 sets of training data set 242 comprises a first image of a subject and a second image of a subject. Each of the 50 sets of training data set 242 may include images of the same subject from different FOVs or images of different subjects.

The first image may be acquired at a first field of view (FOV) and the second image may be acquired at a second FOV different from the first FOV. Each of the first image and the second image may include at least part of a ROI, such that there is overlap of the ROI when the first image and the second image are overlaid. Validator 250 may feed the first image and the second image into the partially trained neural network module 240 and receive a predicted transformation matrix which may be used to stitch the first image and the second image into a single image. In some examples, the validator may also feed the first mask and the second mask into the partially trained neural network module 240. Validator 250 may then compare the single stitched image with the ground truth 248, which may be estimated by an expert (e.g., a manually stitched image of the first image and the second image). Validator 250 may then iteratively adjust one or more parameters (e.g., weights and biases) of the neural network module 240 in order to minimize two or more loss functions based on the predicted transformation matrix, until an error rate decreases below a first threshold error rate. If error between the single stitched image (e.g., based on the predicted transformation matrix) and the ground truth is below the threshold error, the partially trained neural network module 240 may be validated and be determined to be fully trained, the neural network training module 208 may output a trained/validated neural network module 260, and a training stage may end.

Training and implementation system 200 may include an inference module 212, which comprises a trained/validated neural network module 260 (e.g., neural network 240 that has been validated by validator 250 as described above). Inference module 212 may also include instructions for deploying the trained/validated neural network module 260 to generate one or more transformation matrices 270 for one or more sets of input data 222.

In some embodiments, as described in greater detail below in reference to FIG. 5, the one or more new sets of input data 222 may include a first image 224 and a second image 225. The first image 224 and the second image 225 may each be the result of acquired images 220 which have been pre-processed, as further described below. For example, acquired images 220 may be acquired via an imaging device 218, such as an X-ray imaging system, during examination of a subject and may be stored in the image database 214. Similar to the first image 244 and the second image 245 of the training data set 242, the first image 224 and the second image 225 may each be acquired at a different FOV of the subject, each including at least part of a ROI such that there is overlap of the ROI when the first image 224 and the second image 225 are overlaid.

Pre-processing module 216 may also include instructions for pre-processing acquired images 220. Pre-processing acquired images 220 may be similar to pre-processing images of the training data set 242, as described above and in FIGS. 3A-3B. Briefly, acquired images 220 may be pre-processed to minimize variance between image pairs (e.g., the first image 224 and the second image 225) and maximize correspondence for the purpose of image registration. For example, the pre-processing may include adjusting brightness or contrast of one or both of the images so the two images have similar contrast and brightness.

As described above, the input data 222 may be input into the trained/validated neural network module 260 to generate a transformation matrix 270. In some examples, validation of the neural network module 240 to give trained/validated neural network module 260 may indicate the neural network module is sufficiently trained to predict transformation matrices. Additionally or alternatively, the trained/validated neural network module 260 may output linear shift vectors instead of a transformation matrix.

The transformation matrix 270 may include shift vectors indicating, for example, horizontal shifts and vertical shifts, as well as rotation, skew, zooming, and so on, which may be applied to register and stitch the first image 224 and the second image 225. The transformation matrix 270 is thus applied such that images of the image pair (e.g., the first image 224 and the second image 225) may be stitched as a single image without distortion of elements of either of the first image or the second image. As a result, the full ROI, which is partially shown in each of the first image 224 and the second image 225, is fully shown in the stitched image. Further detail regarding application of the transformation matrix for image stitching is described in FIG. 5.

FIG. 3A shows an example workflow 300 for training a TMPN using an input pair, including an image and a mask, to generate a transformation matrix. FIG. 3B shows an example workflow 350 for training the TMPN using an image to generate predicted shift vectors (e.g., of a transformation matrix), and refining the predicted shift vectors using a mask and ground truth shift vectors. FIGS. 3A-3B will be described simultaneously herein.

Acquired images (e.g., acquired images 220 of FIG. 2) may be acquired from an imaging device such as an X-ray imaging system as a raw digital imaging and communication in medicine (DICOM) image 302, though other image formats are within the scope of this application. The raw DICOM image 302 may contain an image acquired from the imaging device and identification data to link the image to a respective patient. The image may have been acquired with collimation methods applied, wherein an X-ray beam of the X-ray imaging system may be confined to an area defined by a user of the X-ray imaging system. Collimation of the X-ray beam may reduce patient dose (e.g., exposure to X-ray beams) to unwanted areas (e.g., a region outside the area to which the X-ray beam is confined). Additionally, collimation may reduce scattering of the X-ray beam by excluding unwanted areas, which in turn may increase image quality (e.g., clarity) of the X-ray image. Images acquired using collimation methods may therefore include a collimation boundary wherein image data within the collimation boundary (e.g., image data of the area where the X-ray beam is confined) may be brighter and have a higher resolution than image data outside the collimation boundary. Workflow 300 and workflow 350 may include collimation removal 304, wherein areas of acquired images (e.g. raw DICOM image 302) outside the collimation boundary are cropped out of the image, wherein the resulting image shows non-collimated image data (e.g., image data within the collimation boundary). The resulting image may include image data including the user-defined anatomical areas of the raw DICOM image 302.

The resulting image may be pre-processed by a pre-processing module 306 to produce an image 308 and segmented by a segmentation module 316 to produce a mask 318. Pre-processing may include adjusting brightness or contrast of the image such that, when input into the TMPN with a second image, the two images have similar contrast and brightness. In one example, image brightness and/or contrast may be a pre-determined quantity, for example, as set by parameters of the TMPN. In another example, image brightness and/or contrast values may be input by a user to the image processing system, and the pre-processing module may adjust brightness and/or contrast of each image to equal input values. Pre-processing may further include additional or different adjustments to be made to images to reduce differences and increase correspondence among images of an image pair (e.g., a first image and a second image with the same ROI and partial FOV overlap) to be input into the TMPN 320.

The mask 318 is configured to identify (e.g., by setting the pixel values to zero in the mask) all pixels of the image 308 outside a ROI. In this way, when the mask 318 is used during training, the CNN (e.g., the TMPN) is informed which pixels of the input images are important for generating the transformation matrix/shift vectors. In this way, the CNN may be trained to rely on the ROI for generating the transformation matrix and not image data outside the ROI.

The pre-processing module 306 and the segmentation module 316 may be a single module, in one example. In another example, the pre-processing module 306 and the segmentation module 316 may be separate modules. In either example, the segmentation module 316 may be excluded and mask 318 may be generated using computer vision or user annotation of the respective image.

In one example, such as shown in workflow 300, the resulting image 308 and mask 318 may be a training pair 310. The training pair 310 may be one of two training pairs of training data set 242 of FIG. 2. In the workflow 300, the training pair 310 may be input into the TMPN 320 along with a second training pair (e.g., generated using workflow 300 or a different workflow) to calculate loss 322.

In another example, such as shown in workflow 350, the resulting image 308 may be input into the TMPN 320 to generate shift vectors 323. For example, when training the TMPN 320, inputting a first image 308 into the TMPN 320 may result in predicted shift vectors 324. Ground truth shift vectors 326, which may be equivalent to the ground truth 248 of FIG. 2, may be compared to the predicted shift vectors 324 to calculate loss 328 of the TMPN 320. Calculating loss 328 may include using the mask 318 to scale loss function values, such that loss 328 is calculated based on image data within the ROI, as defined by mask 318. For example, the mask 318 may be applied to zero out losses associated with areas outside the ROI, so that only loss associated with the ROI, leg bone, spine, etc., will be used for the loss, and thus the parameters of the network will implicitly learn to prioritize these regions. In an example, predicted shift vectors output by the CNN may be used to move an input image, the ground truth shift vectors may be used to move the same image, and then the differences between the first moved image the second moved image may be determined. The mask may then be used so that, instead of comparing all of the differences in pixel values at all regions of the images, only the differences in non-masked regions of the images are considered.

The workflow 300 and the workflow 350 show training of the TMPN 320. For example, workflow 350 may be implemented at least twice to generate two images 308 where each image has a different FOV of a subject, each FOV including a common ROI. Loss 328 may be used to train the TMPN 320 such that predicted shift vectors 324 may be equal to ground truth shift vectors 326. Trained TMPN 320 may then be implemented to generate a transformation matrix based on an input image pair.

A workflow similar to workflow 300 and workflow 350 may be applied for implementation of the TMPN 320, as further described in FIG. 5. However, the masks may only be used during training, e.g., as shown in workflow 300 and workflow 350, and may not be used during inferencing of the trained TMPN. Steps of workflow 300 and workflow 350 prior to inputting the image 308 into the TMPN 320 show a process for a single image. An image pair including two images generated using pre-processing module 216, described above, and having the same ROI with partially overlapping FOVs may be input into the trained neural network module to generate a transformation matrix based on the image pair. The first image and the second image may then be stitched together using the transformation matrix to form a stitched image including the ROI of the first image and the second image. The stitched image may be output on a display device and/or stored in memory.

Workflow 300 and workflow 350 may be examples of training the TMPN 320 using a plurality of training data sets, where each training data set including a pair of images, one mask or a pair of masks generated from the pair of images, and an associated ground truth, and wherein the model is trained by entering the pair of images mask(s) as input to the model or by performing loss scaling with the mask(s). The TMPN 320 may be additionally or alternatively trained using a plurality of augmented training data sets. The augmented training data set may be generated from a respective one of the plurality of training data sets and include an augmented version of the image pair and the same associated ground truth as in the respective one of the plurality of training data sets. The augmented version of the image pair may include augmentations including at least one of localized image gamma adjustments, localized image brightness adjustments, foreign artifacts, and overlap adjustments. A series of augmentations may be used to train the network to be robust in the presence of external objects, stomach gas, variation in dosages, and so on. Augmented training data is further described in FIG. 4. This may allow for robust performance of the TMPN, where the method works for multiple anatomies, dosage variation, and so on.

Training a neural network module may thus include an input comprising a first training pair and a second training pair input into an AI model. Each of the first training pair and the second training pair comprises an image and a mask based on the image. In one example, an ROI of the first training pair and the second training pair is a spine of a subject. For example, the first training pair may show a top region of the spine (e.g., in proximity to subject's shoulders) and the second training pair may show a middle/bottom region of the spine (e.g., in proximity to the stomach and hips of the subject). As described above, the mask is configured to mask pixels of the respective image outside a ROI. For example, the mask of a respective image masks pixels of image showing anatomical structures other than the spine such that convolutions may be performed only on image data depicting the spine when the respective mask is applied to the image in the AI model.

The AI model is herein referred to as the TMPN and may include at least one DL neural network architecture. For example, the DL neural network may be a Siamese twin and Regression Neural Network, a Homography net, a CNN, or another suitable model. The AI model is further trained on two or more losses, which may include grid loss, mean square error (MSE)/root mean square error (RMSE), and location based loss. A combination of one or more loss functions and regularizations may be used to ensure regression. For example, grid loss may be used in conjunction with MSE to increase accuracy of predictions of affine parameters, where grid loss may ensure overall rigidity of the transformation. Because the transformation matrix may include multiple transformations (e.g., linear shift vectors, rotation, zoom, etc.), the application of more than one loss function may be advantageous because different loss functions may increase the accuracy of the prediction of different transformations of the transformation matrix.

The trained AI model (e.g., TMPN) may be implemented to generate a transformation matrix. For example, the transformation matrix may be comprised of shift vectors, which may indicate horizontal or vertical shift, zoom, rotation, skew, and so on, to be applied to the input (e.g., at least one image of the input) such that images of the first training pair and the second training pair may be stitched into a single image.

FIG. 4 shows flow chart of an example method 500 for training the TMPN to generate a transformation matrix based on input data. Method 500 may be an example of the workflows and method of FIGS. 3A-3B for training the TMPN and is described with respect to the image processing system of FIG. 1 configured with the TMPN training and implementation system of FIG. 2. Instructions of method 500 and other methods described herein may be stored in memory of the image processing system and be implemented as described herein. For example, a processor, such as processor 104 of FIG. 1, may be configured to execute method 500 stored in the training module 110 to train the TMPN.

At 502, method 500 includes generating a training data set, wherein, at 504, each training data set includes an overlapping image pair, a mask pair, and a ground truth transformation matrix. Referencing FIGS. 2-3B, the training data set may thus include two training pairs, each with an image and a respective mask. For example, the overlapping image pair may include a first image and a second image with a rigid structure (e.g., ROI) present in both the first image and the second image. The first image and the second image may each show a different FOV of the ROI, where a first FOV of the first image and a second FOV of the second image partially overlap.

The mask pair may include a first mask based on the first image and a second mask based on the second image. For example, a first mask may be generated based on the first image using a segmentation module, such as a segmentation module described in FIGS. 1-3B, by user annotation, or a computer-vision based module. A second mask may be generated based on the second image using one of the methods by which the first mask may have been generated. The same method or different methods may be used to generate the first mask and the second mask. As described above, the mask is configured to mask all pixels of the respective image outside the ROI (if the mask were applied to the respective image).

The ground truth transformation matrix may be generated by a user or other expert in the field and may define a series of horizontal shifts, vertical shifts, zoom, skew, rotations, and so on, which may be applied to at least one of the first image and the second image to stitch the first image and the second image into a single image at the overlap of the first image and the second image.

Additionally, generating the training data set at 502 may include, at 506, generating augmented training data sets with augmented versions of the overlapping image pairs. Augmenting the overlapping image pairs may include one or more of device-related, patient-related, and process-related adjustments applied to one or more of each image (e.g., the first image and the second image). For example, augmentations may include at least one of localized image gamma adjustments, localized image brightness adjustments, inclusion of foreign artifacts, overlap adjustments, and so on. Device-related changes may include local or global intensity changes. Patient-related changes may by inclusion of metal artifacts. Process-related adjustments may be adjustments made to a level of overlap between images. Inclusion of augmented training data sets in addition to training data sets may increase accuracy and robustness of the TMPN, such that the TMPN may accurately generate a transformation matrix when at least one of the input images includes an external object, stomach gas, variation in radiation dosage, and so on. When the images are augmented, the ground truth may not change, such that the ground truth is based on the non-augmented images.

At 508, method 500 includes entering training data, which may include the training data set and the augmented training data set, to an untrained TMPN. At 510, method 500 includes training the TMPN using the entered training data. Training the TMPN includes, at 514, pairing each mask with a respective image to form the training input for the network. In an example, each mask may be concatenated with the respective image and entered as input to the model. In other examples, the mask(s) may be used for loss scaling and only the images may be input to the model.

Training the TMPN further comprises, at 516, calculating loss between an output layer and the ground truth transformation matrix using two or more loss functions. For example, loss functions may include grid loss, MSE/RMSE, and location based loss. The output layer may be a transformation matrix generated by the TMPN and may be comprised horizontal shifts, vertical shifts, rotation, skew, and/or zooming. The ground truth transformation matrix may be generated by user annotation, computer-vision based module, or another transformation matrix generation method other than the TMPN. For example, when generated by user annotation, the images may be manually stitched together and a computer program may be used to generate a transformation matrix which may be used to stitch the images to give a resulting stitched image equal to the manually stitched image. The ground truth transformation matrix may include one or more horizontal shifts, vertical shifts, rotation, skew, and zoom, which, when applied to at least one of the images of the image pairs (e.g., at least one of the first image and the second image) may allow the images to be stitched into a single image including the full ROI (e.g., which is partially shown in the different FOVs of each of the first image and the second image). In this way, the ground truth transformation matrix may be identified as transformations that, when applied, accurately stitch the input images. By calculating loss between the output layer and the ground truth transformation matrix, an accuracy of the output layer transformation matrix, and therefore an accuracy of the TMPN, may be determined.

At 518, method 500 includes updating weights and biases of the TMPN based on loss. In this way, the TMPN may be refined such that generated transformation matrices may be used to accurately stitch input images into a single stitched image including the full ROI. Following performance of convolutions, at 518, weights and biases of the TMPN may be updated based on loss calculated at 516 and based on applications of respective masks. For example, respective masks may be applied to scale loss function values, such that updates to weights and biases are made using loss calculated based on image data within the ROI, as defined by respective masks.

As explained herein, the transformation matrix may include a plurality of transformations (e.g., six transformations). However, in some examples, some transformations may be more important for stitching the images than other transformations. To simplify training, one or more parameters of the transformation matrix may be "masked" in order to remove those parameters from the resultant transformation matrices. For example, in some cases translating an image up or down (y-axis translation) may be prioritized, and in such cases training may be simplified by ignoring/setting to zero transformation matrix parameters which do not affect y-axis translation.

Method 500 returns to start to repeat and further train the TMPN. The TMPN may be trained with a plurality of training data sets and augmented training data sets. In one example, weights and biases of the TMPN may be updated based on loss until error from loss is below a threshold value at which it is determined transformation matrices generated by the TMPN are sufficiently accurate (e.g., the ROI of the stitched image may be interpreted by a user or further method and be used for patient diagnosis or treatment). In another example, weights and biases may be updated for a set number of training data sets and augmented training data sets, e.g., 1000 training data sets, after which it may be determined that the TMPN has been trained and may be implemented to generate transformation matrices used to stitch images.

After the TMPN has been trained, the TMPN may be implemented to generate a transformation matrix for input image pairs, where images of the input image pairs show different FOVs of a ROI where the FOVs partially overlap. FIG. 5 shows a flow chart of an example method 600 for implementing the trained TMPN. Method 600 may be implemented by the inference module 112 of FIG. 1.

At 602, method 600 includes generating input data. Input data may be generated from a first acquired image and a second acquired image, such as the acquired images 220 of FIG. 2 and/or the raw DICOM images 302 of FIGS. 3A-B. The first acquired image and the second acquired image may comprise an overlapping image pair, where a FOV of the first acquired image and a FOV of the second acquired image partially overlap.

Each of the first acquired image and the second acquired image may be pre-processed, as described in FIGS. 3A-3B, to identify the ROI. At 604, the ROI may be identified for the first acquired image and the second acquired image of the overlapping image pair. The ROI may be identified based on a selected imaging protocol, in one example, where a user of the imaging device may select an anatomical structure as the ROI. As described above, the ROI is a rigid structure present in both images. Pre-processing may further reduce differences and increase correspondence among the first acquired image and the second acquired image (e.g., equalizing contrast, brightness, etc.) to give a first image and a second image, respectively. Input data is defined as the overlapping image pair (e.g., the pre-processed first acquired image and pre-processed second acquired image). In examples where the TMPN is trained with one or more masks as input (e.g., as in the workflow of FIG. 3A), the input data that is entered during inference may include one or more zero matrices. For example, each image may be paired/concatenated with a zero matrix so that the TMPN receives expected input based on the training, but the input "masks" do not include information, e.g., the images are input along with one or more matrices of the expected size of the masks but with all zeros instead of meaningful values.

At 610, method 600 includes entering input data into the trained TMPN. For example, the TMPN may be trained by at least one of the methods described in FIGS. 3A-5. Where the TMPN is configured with a CNN, convolutions may be performed on images. The trained TMPN outputs a transformation matrix based on the input data, where the transformation matrix comprises one or more of horizontal shifts, vertical shifts, rotation, skew, and zooming.

At 612, the first image and second image are stitched together based on the transformation matrix. Stitching of the first image and the second image may include applying the one or more horizontal shifts, vertical shifts, rotation, skew, and zooming of the transformation matrix to at least one of the first image and the second image. In one example, a horizontal shift and a zoom to a first frame may be applied to the first image and a vertical shift and a zoom to a second frame (e.g., wider than the first frame) may be applied to the second image. Applying the transformation matrix to at least one of the first image and the second image may allow for the overlap region of the images to align such that the full ROI (e.g., the ROI partially shown in each of the first image and the second image) may be shown in the stitched image in such a way that ROI may not be distorted.

More than two images may be stitched together using the methods described herein. In one example where n number of images may be stitched together using transformation matrices generated as described above, stitching includes, for an image series from image one to image n, the top of the initial stitched image is image one. For the following images, the shift vectors indicate the vertical and horizontal shift between neighboring images. A total length of the stitched image is a summation of a vertical size of images between image one and image n, minus summation of vertical direction shift vectors for images between image one and image n. A left hand side of the stitched image is the right-most left sub-image edge in the initial stitched image. The right hand side of the stitched image is the left-most right sub-image edge in the initial stitched image.

At 614, the stitched image is output, for example, to a display device such as the display device 134, and/or stored on memory, for example, in the image database 114 of FIG. 1. In this way, input images showing partial views of an ROI with different, partially overlapping FOVs, may be stitched together using a transformation matrix generated from the images, such that the ROI is shown in full on the stitched, single image without distortion to the ROI.

The method described in FIG. 5 may be one example of implementing the TMPN to generate a transformation matrix. The method described herein, where images are input into a model trained to output a transformation matrix based thereon, may be implemented using additional or alternate methods. For example, the TMPN may use convolutional blocks along with pooling, normalization, and attention to predict the transformation matrix. Additionally or alternatively, the TMPN may be trained with at least one auxiliary task, for example, to classify an anatomical view, which may be used to refine the TMPN. Addition of an auxiliary task may include an auxiliary output to the network, wherein additional layers of the neural network are targeted to the auxiliary task. In this example, there may be no change in input (e.g., training data is the same as for TMPN training without the auxiliary task). Additional ground truth data may be included for training the auxiliary task. For example, the TMPN may be trained with a linear combination of a first task (e.g., generating a transformation matrix) and the auxiliary task. The auxiliary task may provide additional attention to the input image to increase performance of the first task. The auxiliary task may also solve an additional downstream task, such as view classification (e.g., frontal, lateral, etc.). The addition of an auxiliary task is independent of a network and may be used with any of the deep learning models (e.g., Siamese twin and Regression Neural Network, a Homography net, a CNN, or another suitable model).

In another example, the TMPN may use a single image patch method or a multiple image patch method for predicting a transformation matrix. For example, the single image patch method may be comprised of a single image containing an anatomical marker (e.g., a spinal cord) input into a model, such as a TMPN configured with a CNN or other AI model, and output a single shift vector output. The multiple image patch method may comprise an ensemble of predictions made on multiple image pair patches (e.g., each image may be divided into patches and predictions may be made for each corresponding set of patches) to determine a final transformation matrix using a weighted scheme. In some examples, the weighted scheme may generate a mean transformation matrix, wherein each image holds equal weight. In one example, image pasting may be used to past images in parallel (e.g., instead of a bottom edge of a first image stitched to a top edge of a second image). In this example, multiple transformation matrices may be generated to reduce or adjust for parallax error at different positions of input image pairs.

In some examples, the image processing system, during execution of method 600, may be configured to detect if the user has selected an incorrect scanning protocol for imaging a patient. For example, various imaging system parameters and/or post-image acquisition processing parameters, including image registration and stitching, may be selected based on a scanning protocol, which may dictate the anatomy being imaged (e.g., spine, leg, etc.). If a user has selected a leg protocol but instead images a patient's spine, the image processing system may detect the wrong protocol has been selected based on the segmentation module being unable to identify the ROI (e.g., a leg bone, based on the selected protocol) and hence the TMPN being unable to output a transformation matrix. When the segmentation module cannot identify the ROI, a notification may be output to the user indicating an incorrect scan protocol has been selected, which may enable the user to select the proper scan protocol and rescan the patient with the desired settings tailored for the correct scan protocol.

Conventional methods for auto-stitching images may encounter technical challenges when input images each have differing characteristics, such as different FOVs, lateral motion between images, images generated using different X-ray dosages, presence of non-rigid artifacts, incorrect selection of protocol used to identify ROI, low radiation dose, and so on. The method described herein for using a trained model to generate a transformation matrix based on overlapping images and automatically stitching together images based on the transformation matrix to form a stitched image, includes training the model (e.g., TMPN) such that the TMPN is tolerant of the aforementioned challenges. FIGS. 6A-6D show example images comparing auto-pasted (e.g., stitched) images generated using conventional image auto-pasting methods and images generated by manual pasting.

FIG. 6A shows example images 700 comparing auto-pasting 702 and manual pasting 704 for a pair of X-ray images where lateral motion exceeds lateral motion tolerance of conventional algorithm. Lateral motion may be defined as motion in a horizontal direction. Auto-pasting 702 of images as performed by conventional methods may result in inaccurate image registration in circumstances where lateral motion occurs. For example, a subject being imaged, for example, a patient, may move between capture of a first image and capture of a second image. Lateral movement may be due to physical movement by the subject or movement of an imaging device, such as to frame a region (e.g., shown by circle 706) to be imaged differently or capture a shifted view of the region. When lateral motion exceeds a first shift threshold, for example, 5 cm, conventional image auto-pasting algorithm may result in offset images, as shown by auto-pasting 702. Manual pasting 704 of the same images which have been auto-pasted 702 shows proper alignment of the first and the second image. As shown in circle 706 in auto-pasting 702, the stitched first image and second image may be offset. In manual pasting 704, the stitched first image and second image may be aligned, as shown in circle 706. The herein disclosed method for generating a transformation matrix and stitching together a first image and a second image based on a generated transformation matrix may be trained to accommodate arbitrary lateral shifts. For example, the method described herein may be trained for a broad range of horizontal and vertical shift values (e.g., tolerant of horizontal and vertical shifts greater than 5 cm). In this way, the transformation matrix prediction network may generate a transformation matrix that, when applied to at least one of the first image and the second image, may stitch the first image and the second image such that the region of interest is aligned, similar to that shown by manual pasting 704 of example images 700.

Additionally, training the disclosed method to accommodate arbitrary lateral shifts may allow the method to generate transformation matrices for image pairs (e.g., a first image pair and a second image pair) wherein images of the image pairs have low overlap. For example, low overlap may be approximately 3.5 cm of overlap of a first FOV of the first image and a second FOV of the second image. In this way, the method may be performed while reducing a radiation dose to a patient, for example, fewer images may be captured with low overlap therebetween to image a region captured using more images with greater (e.g., greater than or equal to 4.5 cm) overlap by conventional methods.

FIG. 6B show example images 720 comparing auto-pasting 708 and manual pasting 710 for X-ray images including non-rigid artifacts, such as stomach gas (e.g., shown in circle 712). Conventional methods for auto-stitching images may be search-based and may not be trained to compensate for non-rigid artifacts within images. For example, non-rigid artifacts such as stomach gas may move and change shape/volume between and during image captures. Thus, when a conventional image auto-stitching method is implemented, a first image and a second image may be mis-registered when auto-pasted 708. Structures within the first image and the second image which may be partially or fully obscured by the non-rigid artifact during at least part of image capture may be mis-registered. Manual pasting 710 shows a stitched image of the first image and the second image where the region of interest is aligned despite presence of the non-rigid artifact. The herein disclosed method for generating a transformation matrix and stitching together a first image and a second image based on the transformation matrix may be trained to accommodate non-rigid artifacts, including stomach gas, such that the transformation matrix prediction network may generate a transformation matrix that, when applied to at least one of the first image and the second image, may stitch the first image and the second image such that the region of interest is aligned, similar to that shown by manual pasting 710 of example images 720.

FIG. 6C shows example images 740 comparing auto-pasting 714 and manual pasting 716 for a pair of X-ray images taken using an incorrect protocol selection of a conventional image auto-pasting method. In the example of FIG. 6C, a leg protocol was selected to be used for stitching together a first image and a second image wherein the ROI is a spine. Therefore, a spine protocol may include a feature finder and/or search box extraction for spine features which are not present in the leg protocol. Auto-pasting 714 when the incorrect protocol is selected may result in mis-registration, shown in circle 718. Manual pasting 716 shows a resulting stitched image where the first image and the second image have been correctly registered, shown in circle 718. The herein disclosed method for generating a transformation matrix and stitching together a first image and a second image based on the transformation matrix may be trained to be invariant of selected protocol and be made robust against incorrect protocol selection, for example, during subject scanning image capture, and/or auto-stitching. In this way, the generated transformation matrix prediction network may generate a transformation matrix that, when applied to at least one of the first image and the second image, may stitch the first image and the second image such that the region of interest is aligned, similar to that shown by manual pasting 716 of example images 740.

FIG. 6D shows example X-ray images 760 including foreign objects. A combination of parallax artifact and foreign objects are shown in a first image 722, which is the result of a first image and a second image being stitched together using conventional image auto-pasting methods. For example, a circle 724 shows a metal piece in the X-ray image, which may have been correctly pasted when stitching the first image and the second image. A circle 726 shows mis-registration (e.g., inaccurate pasting) of a vertebra, which may be due to the presence of the metal piece in circle 724. A second image 728 shows multiple foreign objects, for example, metal accessories around the pelvis, which may result in a conventional image auto-pasting method being unable to stitch a first image and a second image into a properly registered final image. Foreign objects may differ from implanted metals or pacemakers, such that an image auto-pasting method may be trained to remove foreign objects from the pasting series in some embodiments. In other embodiments, the image auto-pasting method may intentionally be trained to not remove foreign objects, such as, for example, measurement tools or lead markers, which may to help measurements as defined by the user. The herein disclosed method for generating a transformation matrix and stitching together a first image and a second image based on the transformation matrix may be trained to be invariant of known foreign objects and to instead consider vertebrae when obtaining registration vectors, such as shift vectors of a transformation matrix. In this way, the generated transformation matrix prediction network may generate a transformation matrix that, when applied to at least one of the first image and the second image, may stitch the first image and the second image such that the region of interest is aligned.

Further clinical challenges may be solved by training the transformation matrix prediction network to compensate for dose invariance and low radiation dose. For example, including augmented training data sets with gamma adjustments, as described in FIG. 4, may train the TMPN to be tolerant of dose invariance and low radiation. Additionally or alternatively, training pairs used to train the TMPN may include images captured at different dosages. In this way, the TMPN may be trained to stitch images with varying dose levels (e.g., a first image with a first dose level and a second image with a second dose level).

FIG. 7 shows example images 800 comparing images 810 of input image pairs and a resulting stitched image 820, according to the method of the disclosure. A first image 802 shows an X-ray image of a top portion of a spine and a second image 804 shows an X-ray image of a lower portion of the spine. The first image 802 and the second image 804 are stitched together according to methods described above into a single stitched image 820. Stitched image 820 shows vertebrae of the spine in alignment. Further, a portion 812 of the first image 802 is not shown in the first image 802 region of stitched image 820, as portion 812 and a portion 814 of the second image are overlapping FOV regions (e.g., portion 814 overlaps portion 812) and thus are the region wherein the first image 802 and the second image 804 are stitched.

The technical effect of training and implementing a Deep Neural Network model to generate a transformation matrix based on a first image and a second image, and using the transformation matrix to stitch together the first image and the second image includes reduced operator error, increased accuracy of automatically stitched X-ray image pairs compared to manually stitched images, decreased operator training costs, and increased patient diagnosis efficiency. The method also is trained for low overlap between scans, non-rigid objects, foreign objects, and lateral shifts, such that radiation dose to a patient may be decreased. The disclosed model may thus align and stitch images in the presence of the aforementioned challenges (e.g., low overlap, lateral shift, and so on), which may result in fewer image retakes, which may increase the efficiency of the X-ray system and the computing device executing the model by lowering the number of times images are captured, registered, and stitched.

The disclosure also provides support for a method, comprising: entering a first image of a subject and a second image of the subject to a model trained to output a transformation matrix based on the first image and the second image, where the model is trained with a plurality of training data sets, each training data set including a pair of images, a mask indicating a region of interest (ROI), and associated ground truth, automatically stitching together the first image and the second image based on the transformation matrix to form a stitched image, and outputting the stitched image for display on a display device and/or storing the stitched image in memory. In a first example of the method, the method further comprises: generating the mask based on an image from the image pair with a segmentation model, computer vision, or user annotation. In a second example of the method, optionally including the first example, each training data set further includes a second mask generated based on the other image from the image pair. In a third example of the method, optionally including one or both of the first and second examples, the ROI is a rigid structure that is present in both the images of the image pair. In a fourth example of the method, optionally including one or more or each of the first through third examples, the model is a convolutional neural network (CNN) trained using two or more loss functions. In a fifth example of the method, optionally including one or more or each of the first through fourth examples, each mask is paired with a corresponding image of the pair of images to form a training input to the CNN. In a sixth example of the method, optionally including one or more or each of the first through fifth examples, the mask is used to scale loss function values during training. In a seventh example of the method, optionally including one or more or each of the first through sixth examples, the ground truth comprises a training transformation matrix generated based on the pair of images, wherein the model is trained using two or more loss functions, and wherein the two or more loss functions comprise two or more of grid loss, location-based loss, and mean squared error loss. In an eighth example of the method, optionally including one or more or each of the first through seventh examples, the plurality of training data sets includes data augmentations, the data augmentations including one or more of device-related, patient-related, and process-related adjustments applied to one or more images. In a ninth example of the method, optionally including one or more or each of the first through eighth examples, the transformation matrix comprises one or more of horizontal shifts, vertical shifts, rotation, skew, and zooming. In a tenth example of the method, optionally including one or more or each of the first through ninth examples, the method further comprises: acquiring the first image with an imaging system positioned to capture a first field of view (FOV) of the subject and acquiring the second image with the imaging system positioned to capture a second FOV of the subject, and wherein the first FOV and the second FOV only partially overlap. In an eleventh example of the method, optionally including one or more or each of the first through tenth examples, the imaging system is an x-ray imaging system.

The disclosure also provides support for an image processing system comprising: a deep learning model trained with a plurality of training data sets, each training data set including a pair of images, a pair of masks indicating a region of interest (ROI) in the pair of images, and associated ground truth, and a processor communicably coupled to memory storing the deep learning model and including instructions that when executed cause the processor to: enter a first image of a subject and a second image of the subject to the deep learning model trained to output a transformation matrix based on the first image and the second image, receive, as output from the deep learning model, the transformation matrix based on the first image and the second image, automatically stitch together the first image and the second image based on the transformation matrix to form a stitched image, and output the stitched image for display on a display device and/or store the stitched image in memory. In a first example of the system, the deep learning model is trained using two or more loss functions. In a second example of the system, optionally including the first example, the memory further stores a segmentation model configured to output the pair of masks based on the pair of images.

The disclosure also provides support for a method for an x-ray imaging system, comprising: acquiring, with the x-ray imaging system, a first image of a subject and a second image of the subject, entering the first image and the second image as input to a model trained to output a transformation matrix based on the first image and the second image, wherein the model is trained with a plurality of training data sets that each include a first mask of a first training image and a second mask of a second training image based on a region of interest (ROI) in the first training image and the second training image, automatically stitching together the first image and the second image based on the transformation matrix to form a stitched image, and outputting the stitched image for display on a display device and/or storing the stitched image in memory. In a first example of the method, the first mask and the second mask are generated using a segmentation model, a computer vision-based model, or based on user input. In a second example of the method, optionally including the first example, the model is trained to by entering the first training image, the second training image, the first mask, and the second mask as input to the model or by performing loss scaling with the first mask and the second mask, and wherein each training data set includes an associated ground truth. In a third example of the method, optionally including one or both of the first and second examples, the model is further trained with a plurality of augmented training data sets, each augmented training set generated from a respective one of the plurality of training data sets and including an augmented version of the first training image and the second training image and the same associated ground truth as in the respective one of the plurality of training data sets. In a fourth example of the method, optionally including one or more or each of the first through third examples, the augmented version of the first training image and the second training image includes augmentations including at least one of localized image gamma adjustments, localized image brightness adjustments, foreign artifacts, and overlap adjustments.

As used herein, an element or step recited in the singular and preceded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
   entering a first image of a subject and a second image of the subject to a model trained to output a transformation matrix based on the first image and the second image, where the model is trained with a plurality of training data sets, each training data set including a pair of training images, a mask indicating a region of interest (ROI), and associated ground truth;
   automatically stitching together the first image and the second image based on the transformation matrix to form a stitched image; and
   outputting the stitched image for display on a display device and/or storing the stitched image in memory.

2. The method of claim 1, further comprising generating the mask based on an image from the image pair with a segmentation model, computer vision, or user annotation.

3. The method of claim 2, wherein each training data set further includes a second mask generated based on the other training image from the training image pair.

4. The method of claim 3, wherein the ROI is a rigid structure that is present in both training images of the pair of training images.

5. The method of claim 3, wherein the model is a convolutional neural network (CNN) trained using two or more loss functions.

6. The method of claim 5, wherein each mask is paired with a corresponding training image of the pair of training images to form a training input to the CNN.

7. The method of claim 1, wherein the mask is used to scale loss function values during training.

8. The method of claim 1, wherein the ground truth comprises a training transformation matrix generated based on the pair of training images, wherein the model is trained using two or more loss functions, and wherein the two or more loss functions comprise two or more of grid loss, location-based loss, and mean squared error loss.

9. The method of claim 1, wherein the plurality of training data sets includes data augmentations, the data augmentations including one or more of device-related, patient-related, and process-related adjustments applied to one or more training images.

10. The method of claim 1, wherein the transformation matrix comprises one or more of horizontal shifts, vertical shifts, rotation, skew, and zooming.

11. The method of claim 1, further comprising acquiring the first image with an imaging system positioned to capture a first field of view (FOV) of the subject and acquiring the second image with the imaging system positioned to capture a second FOV of the subject, and wherein the first FOV and the second FOV only partially overlap.

12. The method of claim 11, wherein the imaging system is an x-ray imaging system.

13. An image processing system comprising:
a deep learning model trained with a plurality of training data sets, each training data set including a pair of training images, a pair of masks indicating a region of interest (ROI) in the pair of training images, and an associated ground truth; and
a processor communicably coupled to memory storing the deep learning model and including instructions that when executed cause the processor to:
enter a first image of a subject and a second image of the subject to the deep learning model trained to output a transformation matrix based on the first image and the second image;
receive, as output from the deep learning model, the transformation matrix based on the first image and the second image;
automatically stitch together the first image and the second image based on the transformation matrix to form a stitched image; and
output the stitched image for display on a display device and/or store the stitched image in memory;
wherein during training of the deep learning model, for each pair of training images, each training image and the pair of masks indicating the ROI in the pair of training images are entered into an input layer of the deep learning model and/or each pair of masks is used to perform loss scaling.

14. The image processing system of claim 13, wherein the deep learning model is trained using two or more loss functions.

15. The image processing system of claim 13, wherein the memory further stores a segmentation model configured to output the pair of masks based on the pair of training images.

16. A method for an x-ray imaging system, comprising:
acquiring, with the x-ray imaging system, a first image of a subject and a second image of the subject;
entering the first image and the second image as input to a model trained to output a transformation matrix based on the first image and the second image, wherein the model is trained with a plurality of training data sets that each include a first mask of a first training image and a second mask of a second training image based on a region of interest (ROI) in the first training image and the second training image and an associated ground truth transformation matrix generated based on the first training image and the second training image;
automatically stitching together the first image and the second image based on the transformation matrix to form a stitched image; and
outputting the stitched image for display on a display device and/or storing the stitched image in memory.

17. The method of claim 16, wherein the first mask and the second mask are generated using a segmentation model, a computer vision-based model, or based on user input.

18. The method of claim 16, wherein the model is trained to by entering the first training image, the second training image, the first mask, and the second mask as input to the model or by performing loss scaling with the first mask and the second mask.

19. The method of claim 18, wherein the model is further trained with a plurality of augmented training data sets, each augmented training set generated from a respective one of the plurality of training data sets and including an augmented version of the first training image and the second training image and the same associated ground truth transformation matrix as in the respective one of the plurality of training data sets.

20. The method of claim 19, wherein the augmented version of the first training image and the second training image includes augmentations including at least one of localized image gamma adjustments, localized image brightness adjustments, foreign artifacts, and overlap adjustments.

* * * * *